(12) United States Patent
Costantino et al.

(10) Patent No.: US 9,996,789 B2
(45) Date of Patent: Jun. 12, 2018

(54) METHOD AND APPARATUS FOR MANUFACTURING CUTANEOUS INFORMATION DEVICES

(71) Applicant: Safe & Secure Temporary Tattoo LLC, New York, NY (US)

(72) Inventors: Peter Costantino, Westport, CT (US); Michael Gilvary, Westport, CT (US)

(73) Assignee: Cutaneous Information Technologies LLC, New York, NY (US)

( * ) Notice: Subject to any disclaimer, the term of this patent is extended or adjusted under 35 U.S.C. 154(b) by 0 days. days.

(21) Appl. No.: 15/295,144

(22) Filed: Oct. 17, 2016

(65) Prior Publication Data

US 2017/0081561 A1    Mar. 23, 2017

Related U.S. Application Data

(63) Continuation-in-part of application No. 14/860,646, filed on Sep. 21, 2015, now Pat. No. 9,489,466, and (Continued)

(51) Int. Cl.
*G06K 19/077* (2006.01)
*G03G 15/01* (2006.01)
(Continued)

(52) U.S. Cl.
CPC .......... *G06K 19/07722* (2013.01); *C09J 7/21* (2018.01); *G03G 15/01* (2013.01); (Continued)

(58) Field of Classification Search
CPC .......... G06K 19/07758; G06K 19/041; G06K 19/07726; G06K 7/1447; G06K 19/07749; B41M 3/12; B41M 5/0256; B41M 2205/10; G09F 21/02; G09F 3/0297; A61B 90/94; Y10T 428/1471; Y10T 428/1476;
(Continued)

(56) References Cited

U.S. PATENT DOCUMENTS 2,578,150 A * 12/1951 Rathke ................... B44C 1/175
156/155
4,529,654 A * 7/1985 Drum .................... B44C 1/175
156/234
(Continued)

*Primary Examiner* — Claude J Brown
(74) *Attorney, Agent, or Firm* — Handal & Morofsky LLC

(57) ABSTRACT

A frangible single-use cutaneous information device is printed on a support sheet captured by an adhesive layer and adhered to the skin by the adhesive layer. A skin safe contrasting printed dye is deposited onto a release paper layer allowing the dye construct to be released from the paper and applied to the skin. A clear coat layer can also be applied before or after the dyes are deposited on the paper to protect the outer layer. A single apparatus to be applied at point of service using variable data make such a device includes a means for receiving a perforated sheet, an electrostatic image forming and transferring device, a member for fusing the image to the perforated sheet, an adhesive applicator positioned to apply adhesive to the image, and a transport and joining structure that transports the perforated protective sheet and joins it to the perforated sheet at a position overlying the adhesive.

21 Claims, 3 Drawing Sheets

Related U.S. Application Data a continuation-in-part of application No. 14/862,033, filed on Sep. 22, 2015, now Pat. No. 9,519,724, and a continuation-in-part of application No. 14/862,081, filed on Sep. 22, 2015, now abandoned.

(60) Provisional application No. 62/242,973, filed on Oct. 16, 2015, provisional application No. 62/357,240, filed on Jun. 30, 2016, provisional application No. 62/357,252, filed on Jun. 30, 2016, provisional application No. 62/359,104, filed on Jul. 6, 2016, provisional application No. 62/365,988, filed on Jul. 23, 2016, provisional application No. 62/375,892, filed on Aug. 16, 2016, provisional application No. 62/377,786, filed on Aug. 22, 2016.

(51) Int. Cl.
*G06F 17/30* (2006.01)
*G06K 7/14* (2006.01)
*G06Q 50/12* (2012.01)
*G06K 19/04* (2006.01)
*G06K 7/06* (2006.01)

(52) U.S. Cl.
CPC ..... *G06F 17/30879* (2013.01); *G06K 7/1447* (2013.01); *G06K 19/041* (2013.01); *G06K 19/0776* (2013.01); *G06K 19/07749* (2013.01); *G06Q 50/12* (2013.01); *G16H 10/65* (2018.01); *C09J 2400/283* (2013.01)

(58) Field of Classification Search
CPC .. G06F 17/30879; G06Q 50/12; G16H 10/65; C09J 7/21
USPC .......................................................... 235/441
See application file for complete search history.

(56) References Cited

U.S. PATENT DOCUMENTS

| | | | |
|---|---|---|---|
| 5,958,560 A * | 9/1999 | Ewan | B41M 3/12 427/149 |
| 6,074,721 A * | 6/2000 | Moore | B41M 3/12 156/89.11 |
| 6,264,786 B1 * | 7/2001 | Cromett | B44C 1/1733 156/230 |
| 6,299,967 B1 * | 10/2001 | Collins | B41M 3/12 428/32.12 |
| 7,517,571 B2 * | 4/2009 | Funke | B44C 1/1758 428/195.1 |
| 7,988,199 B2 * | 8/2011 | Welsh | G09F 3/00 281/5 |
| 2003/0152733 A1 * | 8/2003 | Wittmeyer, Jr. | B41M 3/12 428/40.1 |
| 2003/0215593 A1 * | 11/2003 | Morgan | A23G 9/283 428/40.1 |
| 2004/0091659 A1 * | 5/2004 | Banks | G06K 19/041 428/41.8 |
| 2006/0068146 A1 * | 3/2006 | Marks, III | B41M 5/504 428/40.1 |
| 2007/0029377 A1 * | 2/2007 | Hinckley | G06K 19/041 235/380 |
| 2008/0220195 A1 * | 9/2008 | Henshaw | G09F 3/10 428/41.8 |
| 2011/0025040 A1 * | 2/2011 | Dominguez | G09F 3/00 283/75 |
| 2011/0119187 A1 * | 5/2011 | Heeter | G06Q 20/382 705/44 |
| 2011/0268873 A1 * | 11/2011 | Blette | A61K 8/345 427/147 |
| 2012/0037291 A1 * | 2/2012 | Goolishian | B44C 1/1758 156/62 |
| 2014/0185067 A1 * | 7/2014 | Kawano | H04N 1/50 358/1.9 |
| 2014/0354749 A1 * | 12/2014 | Garbacz | B41M 5/38292 347/172 |
| 2015/0053759 A1 * | 2/2015 | Cahill, Jr. | G06K 19/06009 235/380 |
| 2016/0027042 A1 * | 1/2016 | Heeter | G06Q 30/018 705/14.47 |
| 2016/0073759 A1 * | 3/2016 | Malafarina | A45D 29/001 132/200 |

* cited by examiner

Blank Sheet Coated with Release Agent

Sheet with Image

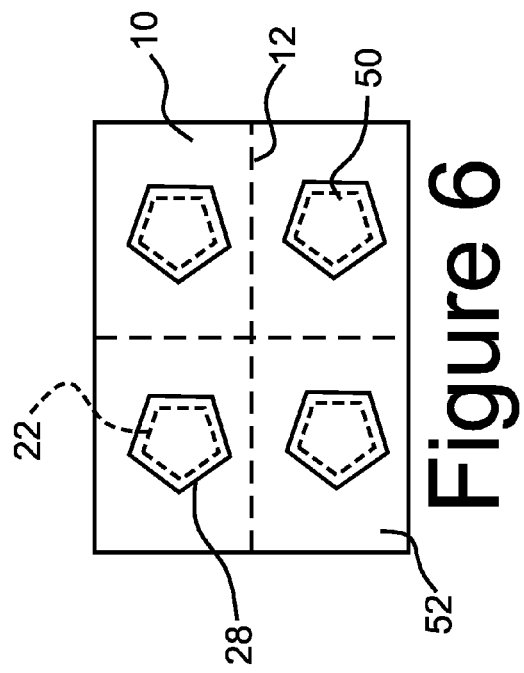
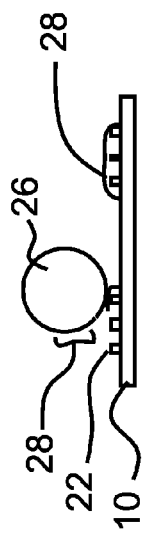

METHOD AND APPARATUS FOR MANUFACTURING CUTANEOUS INFORMATION DEVICES

TECHNICAL FIELD

The invention relates to apparatus and methods for manufacturing a ready to apply cutaneous information device suitable for adhesion to human skin and able to be read by an optical electronic device, electronic devices using near field communication technology such as RFID and bluetooth, data processors such as circuits, microchips and microprocessors and security components for authentication.

CROSS REFERENCE TO RELATED APPLICATIONS

This application claims priority to U.S. Provisional Application No. 62/242,973, entitled, METHOD AND APPARATUS FOR MANUFACTURING CUTANEOUS INFORMATION DEVICES, filed on Oct. 16, 2015. This application also claims priority of International Application No. PCT/US2015/051289, entitled, SECURITY AND ACCOUNTING INFRASTRUCTURE, AND ASSOCIATED CUTANEOUS INFORMATION DEVICE AND METHOD, filed on Sep. 22, 2015, as well as applications U.S. patent application Ser. No. 14/860,646, TRANSPORTATION AND RESORT INFRASTRUCTURE, AND ASSOCIATED CUTANEOUS INFORMATION DEVICE AND METHOD, filed Sep. 21, 2015, U.S. patent application Ser. No. 14/862,033, TEMPORARY CUTANEOUS INFORMATION DEVICE AND ASSOCIATED METHOD AND MULTI-PATIENT TREATMENT INFRASTRUCTURE, U.S. patent application Ser. No. 14/862,081, TEMPORARY CUTANEOUS INFORMATION DEVICE, ASSOCIATED METHOD AND RESORT INFRASTRUCTURE both filed on Sep. 22, 2015, U.S. Provisional Application No. 62/357,240, entitled, TRANSITIONS OF CARE INFORMATION DEVICE, filed on Jun. 30, 2016, U.S. Provisional Application No. 62/357,252, entitled, SKIN APPLIED POINT OF SERVICE PREPARATION DEVICE PROCESS AND DESIGN TECHNICAL FIELD, filed on Jun. 30, 2016, U.S. Provisional Application No. 62/359,104, entitled, SKIN APPLIED POINT OF SERVICE PREPARATION DEVICE PROCESS AND DESIGN TECHNICAL FIELD, filed on Jul. 6, 2016, U.S. Provisional Application No. 62/365,988, entitled, METHOD FOR THE BIOCOMPATIBLE SKIN SAFE APPLICATION OF MULTIPLE COLOR IMAGES TO THE SKIN, filed on Jul. 23, 2016, U.S. Provisional Application No. 62/375,892, entitled, METHOD FOR BIOCOMPATIBLE SKIN SAFE APPLICATION OF ONE OR MORE COLOR IMAGES TO THE SKIN USING SUBLIMATION PRINTING, filed on Aug. 16, 2016, and U.S. Provisional Application No. 62/377,786, entitled, IMPROVED VISUALLY, OPTICALLY AND ELECTRONICALLY READABLE DEVICE FOR DURABLE AFFIXATION TO THE SKIN, filed on Aug. 22, 2016, the disclosures of which are incorporated herein by reference.

BACKGROUND OF THE INVENTION

Today there is a wide range of products on the market facilitating the temporary application of decorative images to the skin. The same are generally commercially manufactured using a screen printing process, and may comprise temporary tattoos for children or other products meant for adult consumers and more in the realm of jewelry, however these methods can not be manufactured at point of service with variable data input. Products for creating homemade temporary tattoos are also available on the market, generally centering on the use of a computer and an inkjet or laser printer to print an image on a specialized sheet designed to receive the image from the inkjet printer and allow its transfer to a second adhesive bearing sheet to allow application to the skin of the wearer. In principal, such specialized sheets may be used to receive images from inkjet or laser printers, however, home systems use printers, toners and inks are not safe for skin contact.

Temporary tattoos are well known for aesthetic purposes, and generally include an ink transfer. Examples of such temporally tattoos are found in U.S. Pat. Nos. 3,898,357, 5,421,765, 5,578,353, and 5,601,859, the disclosures of which are incorporated herein by reference. Specifically, U.S. Pat. No. 4,522,864 to Humason et al. provides general background on the structure of temporary tattoos, as well as fabrication materials and methods.

U.S. Pat. No. 6,264,786 to Cromett (Mattel) issued Jul. 24, 2001 shows a user-created temporary tattoo structure and method of creating a custom temporary tattoo using a PC and printer, in which the user prints an image on a coated sheet, then covers the image with a film, attaches the film/image/coating laminate to skin, and removes a backing sheet to release the image on the skin. This allows a user to create an image on a computer, print the image using a computer printer, and then safely apply the image to human skin.

The use of cutaneously supported images as identifiers together with cooperating devices, systems, apparatus and methods in tracking, for the purposes of the security, safety, billing and other servicing of patrons at travel, recreational and other facilities, such as an airline terminal, resort, convention center, hospital or hotel, is disclosed in published U.S. Patent Application Publication Nos. US20160103925, US20160103962 and US20160104062.

Despite the merits of the concept, conventional temporary tattoos have drawbacks. They are semi-translucent and print information appearing thereon can be difficult to read, especially on dark skin. A more opaque skin applique with high contrast information would be more desirable. These commercially made tattoos are also done using a large screen printing or digital printing process that is done in a factory or industrial setting. This does not make it possible to generate the tattoo with readable information both visually and machine read in real time at point of service with variable data input. Desktop printers can create temporary tattoos at home, but the ink being used for the at home printers are not safe and the ability to print with a contrasting background is only available in the laser printer market, and in this sector the toners are not safe for skin contact. Moreover, temporary tattoos are not sometimes durable enough. In a protected environment it can last a few days. In a theme park the pigments can last at most a few hours in a water park or at the beach and often it lasts a few minutes before beginning to degrade.

In addition, many temporary tattoos typically must be wetted with a warm wet sponge, washcloth or paper towel, and then dried thoroughly. This can take several minutes and is not easy to do with small, excited children seeking to enter an amusement park, and the parent must have access to a restroom inasmuch as the water and sponge cannot be included in the packaging. Using temporary tattoos in this environment can slow the admission process thereby making it operationally undesirable.

Temporary tattoos may be allowed to remain on the skin for various lengths of time, ranging from just a few minutes to several days, depending on the whims of the wearer of the tattoo, the amount of washing and rubbing to which the tattoo is exposed, the amount of hair on the individual, the amount of sweat produced while being warn and the durability of the tattoo. Because of the potentially extended time of contact between the tattoo and a wearer of the tattoo, there is a realistic concern that the inks, toners or other materials used could be absorbed through the skin, resulting in possible injury to the wearer of the tattoo. Accordingly, the construction of temporary tattoos according to the prior techniques has been limited to the use of carefully selected, non-toxic inks. There is a need for temporary tattoos that may be made safely with a variety of inks, including those inks that may not be completely non-toxic, as may be found in some computer printers which durable enough to sustain long term wear, the elements and the hair and sweat of the skin and which can be manufactured at the point of service using variable data. Variable data is data that is not known prior to the manufacturing process. This data is usually discovered at point of service and can be unique and different for each individual.

There is a need for a printing system to print out a frangible, non toxic skin applied (cutaneous in the manner of a temporary tattoo) information device using a desktop sized printer which allows the device to be applied to an individual at the point of service with variable data for applications such as hotel industry, medical industry, travel industry and other such industries where on the spot temporary identification is desired. Point of services implies the device must be the appropriate size to fit into the environment of application, must be generated using variable data and applied in reasonable time frame as to not disrupt the current operations. This device must have visual and machine-readable information, which will serve as a repository for information and a unique identifier.

SUMMARY OF THE INVENTION

In accordance with the invention, a method and apparatus are provided for a single step manufacture of a frangible, one time use cutaneous information device (CID) using variable data. The present application relates to labeling structures adapted to be adhered to the skin in much the manner of a temporary tattoo.

Such operation requires a printing step, a joining step or application of adhesive, placement of a protective layer, cut out step and an application step. While this is feasible on an industrial level, there is a need for a simplified method to manufacture customizable at point of service devices.

To create point of service and single step printing of frangible, non-transferable CID with variable data input several factors need to be considered. As the inventive CID is meant to include a visual identification information like name or date of birth plus machine-readable code, such as a barcode, QR Code or Datamatrix, there is a need for a contrasting (preferably white) background needed so that the information is actually machine readable. The contrasting layer can include ink, a substrate or white adhesive. The ink or toner must be skin safe. The printer can also add in the adhesive that can be a separate layer or interspersed with the ink. In preferred embodiments, perforated paper is used so that the CID can be easily removed from the sheet for application and can also have a substrate that when perforated can perforate the substrate as well. In preferred embodiments, the adhesive is directly added to the toner or ink cartridges so no additional step is needed, furthermore metal ink would be available for printing RFID, tagents and other security features like UV and nano-RFID chips for authentication. The printer would produce a CID which has excellent resolution and print quality on demand on a non-industrial setting.

Presently, there is no biocompatible system that can print variable data at home that is a skin safe with adhesive that lasts 21 days. Such a system is particularly useful when there is a need for a white background not only to draw a contrast between words and lettering but for the easy identification of quadratic codes, bar codes and datamatrix codes. The frangible, machine readable device is particularly useful in settings where identification and linkage to a remote system is needed for not only immediate identification but also for safety reasons.

BRIEF DESCRIPTION OF THE DRAWINGS

The operation of the inventive method and apparatus will become apparent from the following description taken in conjunction with the drawings, in which:

FIG. 5 illustrates the application of adhesive in the context of the present invention;

FIG. 6 illustrates the adhesive applied to the sheet carrying printed information;

FIG. 7 is a schematic cross-sectional view illustrating adhesive applied to the sheet carrying printed information;

DETAILED DESCRIPTION OF THE PREFERRED EMBODIMENTS

Figure 2:
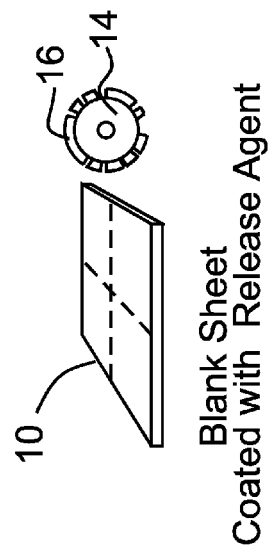
FIG. 2 schematically illustrates a drum carrying a toner image for transfer to the sheet illustrated in FIG. 1.

The printing method provides a durable non-transferable CID (cutaneous identification or information device) that can last weeks even in an aquatic or other more extreme environments, and yet which can be intentionally removed quite easily although removal will destroy the device and render it illegible and inoperable.

The method comprises printing a combination of skin safe pigment (ink, toner) and skin safe adhesive for application to skin in the manner of a temporary tattoo. A skin-safe color image comprising ink and adhesive is printed on a support sheet, which is a carrier sheet having a release agent. The dye is deposited onto the release paper layer using a printer. When the dye is in a solid state, the adhesive is added as seen in FIG. 5. The paper will have a release layer, which will allow the dye construct to be released from the paper and applied to the skin. In accordance with the invention it is contemplated that a white printed dye will be used. Such dye may be a fifth dye in the printing process or the white dye may replace one of the existing colors in the printer, with two of the remaining existing colors being selected, for example to give a good simulation of a range of skin tones, as well as a distinctive and wide range of colors.

A white layer may be applied to enhance contrast or otherwise improve image readability. Alternatively, color pigments may be covered by a substrate pigment layer which is substantially contiguous with the entire area of the image, for example a white substrate pigment layer, which provides the dual functions of a) providing a contrasting background for the image formed by the color pigment, b) shielding the skin from the color pigments to enhance safety and hypoallergenic properties, and c) possibly providing added sunscreen or UV protection.

A clear coat layer can also be applied before the dyes are deposited on the paper so that when the construct is applied to the skin the most outer layer, the one exposed to the elements, will be protected by a clear coat thereby extending the life of the identification device. With this process, a clearer image, visible on all skin tones, with a higher resolution and a more durable construct can be applied to the skin.

The substrate can be clear—in which case the portable printer will have the ability to print in white. The printer will lay down a white layer than apply the design in color resulting in a visually readable CID, which is ready to apply. In an alternative embodiment, the adhesive and or the substrate will have a white pigment serving as the contrast necessary to read the data on the CID. A pigmentary or nano sized colorant particle is incorporated into a fusible material, such as a fusible polymeric or resinous material of a type currently employed or suitable for the manufacture of laser printer toner, to form color toners, and white toners. In accordance with the invention, toners are fabricated using colorants, for example pigmentary and nano-sized pigments that are biocompatible with human skin over relatively long term exposure periods, for example in the range of 5 to 21 days. Multiple skin-safe color inks or toners including white and black may be adhered to the skin to form an image. Black can be created by melding the colors together or by using black particles.

In preferred embodiments, the printer will also have the ability to print in metallic or conductive ink, deposit a dye and thereby create a working RFID, circuit, BLUETOOTH® or other non-contact communication device. The printer will also program the dye during the printer process or use a unique identification code that is preprogrammed on the dye before the printer applies to the CID. Data processors such as circuits, microchips and microprocessors can be added to the device in conjunction with a conductive ink to create a skin wearable computer-processing unit. Security components such as holograms can be added in the final step for authentication.

Figure 1:
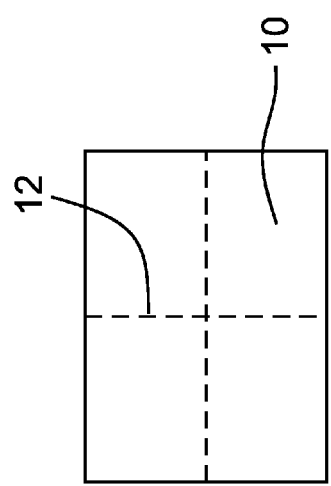
FIG. 1 illustrates a perforated sheet suitable for receiving a cutaneous information device in accordance with the present invention.

Referring to FIG. 1, a sheet 10 suitable for the printing of temporary tattoos is perforated into four quarters by perforations 12. The sheet is preferably perforated to allow for easy tearing. For use with a portable printer, sheet 10 may be long and narrow so it prints out like a receipt and each CID can be torn as it comes out of the printer and they would be printed in a single file line. Sheet 10 could have patterns, designs, or other security features for authentication. In preferred embodiments, sheet 10 could be can be coated with a very thin substrate so that when the CID is transferred to the body the outer most layer is a protective coating. In an alternative embodiment, sheet 10 could be an all-encompassing carrier sheet so that the only part that needs to be added is the ink—once this ink is added the CID would be ready to apply. Sheet 10 could be pre-treated with nano RFID that would then be transferred to the individual during the application process or have RFID already on it where the printing is done on top of the RFID. Sheet 10 could further be pre-treated with silver or copper ions for antibacterial properties or treated with hypoallergenic properties. The sheet is preferably perforated to allow for easy tearing. For use with a portable printer, sheet 10 may be long and narrow so it prints out like a receipt and each CID can be torn as it comes out of the printer and they would be printed in a single file line. Sheet 10 could have patterns, designs, or other security features for authentication. In preferred embodiments, sheet 10 could be can be coated with a very thin substrate so that when the CID is transferred to the body the outer most layer is a protective coating. In an alternative embodiment, sheet 10 could be an all-encompassing carrier sheet so that the only part that needs to be added is the ink—once this ink is added the CID would be ready to apply. Sheet 10 could be pre-treated with nano RFID that would then be transferred to the individual during the application process or have RFID already on it where the printing is done on top of the RFID. Sheet 10 could further be pre-treated with silver or copper ions for antibacterial properties or treated with hypoallergenic properties.

Figure 3:
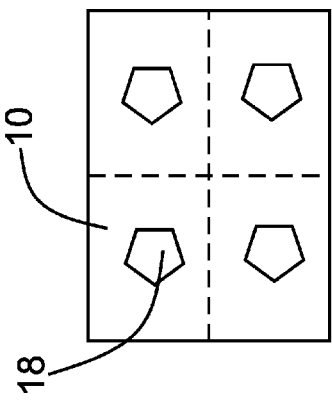
FIG. 3 illustrates a sheet with identification information disclosed thereon.
Figure 8:
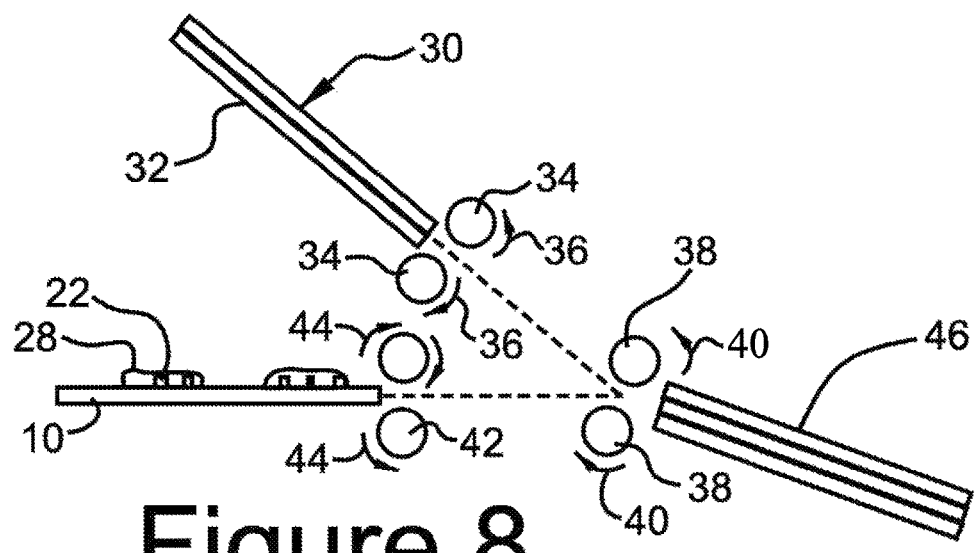
FIG. 8 illustrates the sheet illustrated in FIG. 6 being covered with a protective member.
Figure 9:
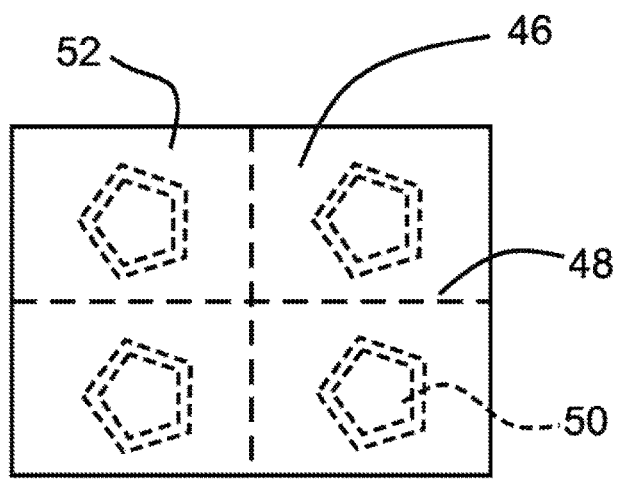
FIG. 9 illustrates a finish sheet of cutaneous information devices comprising a base layer with printed matter and a protective sheet ready to be broken apart into a number of separate devices.

Using a conventional xerography process, sheet 10 is passed under a roller 14 carrying and electrostatically transferred array of toner 16 corresponding to an image. See FIG. 2. Toner 16 is transferred to sheet 10 to form image 18, as illustrated in FIG. 3.

In accordance with the invention, image 18 is formed from at least two toners, for example a black toner and a white toner, in order to provide high contrast for reliable reading of a UPC code, datamatrix, QR or other machine-readable code to be included in the inventive cutaneous information device. While, in principle, printing of a single color to be applied to the human skin resulting in a visual display of a machine-readable code with human skin of the background is suitable for reading by machine, the use of a printed white background form by white toner is preferred so that the machine-readable UPC, datamatrix, QR or other code presents a simple and highly reliable black and white image. This is particularly important in the case of applying the image to human skin, where skin tones may range from very pale to very dark.

The colored design on the CID when applied sits on an opaque brightly contrasting background making it more visible. The CID is relatively robust and durable as the multilayered construction protects the colored pigments from the skin and when used with the optional but preferred third clear outer layer, from outside elements. The CIDs can last weeks in the harshest environments (even water parks), and yet can be removed at will quite easily.

In a preferred embodiment, The CID would comprise a white layer that would interface with the user's skin and a second colored layer with a desired designs or printing. The white layer and optional adhesive layer or clear layer can serve as a protective barrier. The skin interfacing white protective barrier, prevents the colored inks that may or may not be biocompatible with a user's skin even if the colored pigments are safe for skin contact given the various potential sensitivities of different people. The white barrier, also may prevent the colored pigments from being absorbed into the skin and being distorted or fading over time. Furthermore, the white layer is also provides a contrast background to make the design easier to see. The colored pigments would be conducive to being printed on the white layer and would preferably but not necessarily biocompatible. The colored pigments would also be hydrophobic and durable so as to not wash off. The optional clear or transparent layer would cover the colored pigment layer providing a barrier against the outside elements. The pigment layer would comprise a biocompatible pigment, the colored portions would preferably comprise biocompatible pigments treated to be to usable to be in used with a conventional printer. The transparent coating or adhesive layer would comprise materials such as biocompatible pressure sensitive and structural adhesives and sealants. Malleable adhesive is preferable as it can mold to around the pigment particles and the pores of the skin. Additionally the transparent layers would add another barrier or protection for the CID to extend wear. This would include drying adhesives, pressure sensitive adhesives, contact adhesives, and hot adhesives.

The toner cartridges or ink wells and the like can be filled with the specialized adhesive materials and pigment. The paper is treated with a release layer that allows the toner with adhesive particles to be released from the paper and activate the adhesive on to the skin in a single step when water is applied.

In accordance with a particularly preferred embodiment of the invention, CIDs can be manufactured using glow-in-the-dark components or UV activated under a black light as well as a security measure, to provide for identification of a user in the dark. This has the advantage of making it unnecessary to disturb users by turning on lights during sleep. Moreover, it may also save time in emergency situations. The CIDs may be made to glow in the dark by several techniques. For example, glow-in-the-dark pigments may be mixed into the adhesive, which remains on the skin of the user while the badge is being worn. Such phosphor pigments may be of any color, and may be used for color-coding purposes. Green phosphors are preferred for their longer persistence, although blue phosphors have the advantage of brighter light emission.

It is also possible to mix glow-in-the-dark phosphor pigments with transparent thermoplastic toner material to make a glow-in-the-dark toner for laser printers. Additional versatility may be achieved by using transparent tinted red, blue and yellow phosphorescent toner pigment formulations with a black pigment formulation. In this case the black pigment formulation would be of conventional design and would be used to depict alphanumeric and/or image data, while the glow-in-the-dark pigments may be used for tinted backgrounds, identification background patterns, and so forth. Still another possibility is to utilize a five-toner cartridge laser printer where four of the toner cartridges are of conventional design and the fifth toner cartridge contains a phosphorescent toner formulation, which acts as a light source to improve visibility in the dark.

Figure 4:
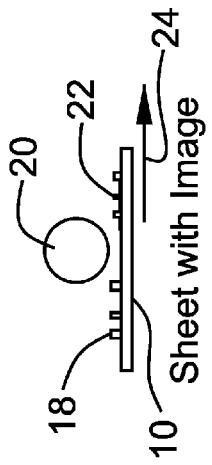
FIG. 4 illustrates the toner fusing operation.

As shown in FIG. 4, the transferred image 18 is used by a heated roller 20 to form a fused image 22, as sheet 10 is advanced in the direction of arrow 24. Referring to FIG. 5, sheet 10 carrying the fused image 22 is then passed under a roller or screen-printing process 26, which applies adhesive 28 over an area substantially corresponding to the area taken up by fused image 22, as is most clearly illustrated in FIG. 6. After the adhesive is applied, a protective member may, in accordance with a preferred embodiment, the applied over the adhesive. In an alternative embodiment, the ink and adhesive are dispensed together rather than being applied in separate layers. In addition to ink and adhesive, rollers 14 and 26 could be used to print other elements such RFID, BLUETOOTH®, non contact communication devices, antennas, copper or silver for antimicrobial properties, and glow in the dark properties.

In accordance with the invention, it is desired that the inventive process results in the production of a plurality of cutaneous information devices which may be broken apart from a larger sheet, for example a standard 8.5"×11" letter size sheet of paper or printed on a continuous roll. Accordingly, the protective layer may be a plastic for plastic coated paper 30 the same size as sheet 10, and including a protective release coating 32. Plastic coated paper 30 would also be perforated, with perforations, which substantially overlap perforations 12 on sheet 10.

Plastic coated paper 30 is fed, for example, by rollers 34 rotating in the direction of arrows 36 toward joining rollers 38 rotating in the direction of arrows 40. Similarly, sheet 10 with adhesive 28 and deposited fused image 22 is fed by rollers 42 rotating in the directions of arrows 44 toward joining rollers 38. Joining rollers 38 then join plastic coated paper 30 to sheet 10 to form unitary member 46, which comprises sheet 10 and plastic coated paper 30 with perforations 48 substantially overlying perforations 12.

When it is desired to use the inventive cutaneous information device, individual quarters of sheet 10 each carrying a single cutaneous information device 50 may be separated from sheet 10. The separated quarter, because it includes a large peripheral area 52 without adhesive, maybe easily peeled resulting in removal of the quarter of the adhesive protective layer, and leaving behind a quarter of sheet 10 with a cutaneous information device 50 deposited thereon, with its associated adhesive exposed.

The quarter of sheet 10 with a single cutaneous information device 50 deposited thereon, and is exposed adhesive layer may then be applied to the skin, for example a patient in the hospital or a vacation or at a resort as an identification device. The quarter of sheet 10 may then be wet with a sponge, allowing the paper to be separated from the ink forming image 22, allowing adhesive 28 (positioned between the skin of the individual and the ink forming image 22) to secure the ink forming image 22 to the skin in the manner of a temporary tattoo.

While one printing method is disclosed above, an alternative embodiment, the paper does not have to be quarters or any set amount per page or 8.5×11 and could in any format, for example, with a roll format. In preferred embodiments, the printer is small in size, such as a hand held or clipped to the hip device. The device needs only to be large enough to print the CID, hold the necessary components for color printing.

There are multiple printing methods that may be adapted to print the CIDs at the point of service or outside of an industrial setting. Some of those methods for portable printing engine include inkjet, continuous (CIJ), drop-on-demand (DOD), thermal DOD, piezoelectric DOD, Offset printing, Rotogravure, Flexography, Letterpress printing, Screen-printing, Electrophotography, Transfer-print, SOHO inkjet photo printing, Fine Art Inkjet Printing, Memjet, Edgeline, and Waterjet among others. In applications where the identification is meant to expire the CID can be generated with this type of printing technology where the ink will fade by design rendering it unreadable.

Laser Printing as defined in other patent applications electrostatic digital printing process. Laser has many advantages including the ability to print in white and anti-counterfeiting technology to name a few. Similarly the Tonejet process is an electrostatic drop-on-demand deposition technology that enables high-quality images to be printed onto virtually any type of absorbing or non-absorbing substrate at high speed. Any one of these systems can utilize a contiguous ink system if configured in a stationary setup.

Dye-Sublimation Printing uses heat to adhere the ink to the substrate by releasing the ink from a ribbon. Dye-Sublimation printers also have an overcoat as well, which can further protect the image being created.

In an alternative embodiment the last clear layer would be replaced with an adhesive layer making this layer the one that comes in contact with the skin. This adhesive can be pressure sensitive, activated by a solvent, water, UV light, heat or any other method of adhesive activation.

As mentioned above, in an alternative embodiment the adhesive particles will be included in the formulation of the pigment, toner, dye or ink. Therefore there will be no need to add an additional adhesive layer and these adhesive particles which will bond the CID to the surface of the skin can be activated with a solvent, water, UV light, pressure, heat or any other adhesive activation process.

In an alternative embodiment the present invention to provide a CID (cutaneous identification or information device) with a white (or other solid color) background, colored contrasting background and clear third outer layer which is the layer that will come in contact to the skin when applied.

In another embodiment, one of the cartridges in the printer will contain metallic or conductive ink that can be used to print the antenna of an RFID device, BLUETOOTH®, radio or any other section of a circuit where metallic materials are necessary. With the metallic cartridge a ready-made CID can be generated from a printer with a workable RFID antenna or any other form of noncontact communication requiring a circuit with metallic materials. In a preferred embodiment, the RFID antenna or the like printed in the printer will also be MRI compatible. In an alternative embodiment as described in previous disclosures, RFID devices will be included in the construct. These RFID devices will be printed using a metallic or conductive ink printer, rolled on using a pressure roller or can be found in the formulation of the dyes. In this process one cartridge in the printer will include metallic inks. These metallic inks can be used essentially print the antennas as part of the CID construct.

These metallic inks could also be MRI compatible Non-ferromagnetic metals such as titanium, cobalt-chromium alloys, stainless steel, aluminum, brass, copper, and many others. Silver, copper and many other materials also have metallic particles which are known to have antibacterial and anti microbial properties. These metallic particles can also be included in the dye to create these anti microbial and anti bacterial properties with the CID.

In an alternative embodiment, the printer could apply inks or other materials or substances to the CID to be used in connection with Laser, IR, UV light or any electromagnetic technology. Bioluminescent ink (light emitting from organic material), inks to print an OLED organic light-emitting diode (OLED) and other such materials can be used to interact with the device in any number of environments to enhance the capability or effectiveness of the product and also be used as a method of applying the device to an individual.

An alternative embodiment of the invention would have the tattoo function would include using a perforated barrier sheet that would make more like a sticker, less like a tattoo and cause it to break apart when the structure is removed or attempted to be removed making the CID impossible to transfer. Sheet 10 could be in the form of a carrier sheet with adhesive and an extremely thin substrate and that device is printed on directly then peeled and apple to the skin directly and white so that when it is transferred like a sticker the white layer is already present and does not need to be applied by the printer. This embodiment would be good in disaster situations or any other scenario where frangibility or enhanced security is not as important. Possible materials for use include double layer 3M' Breathable Polyurethane Tape, as will be described. This particular tape is well suited for skin application since it is breathable yet provides a liquid barrier and the hypoallergenic acrylate adhesive provides for excellent "quick stick" to skin or other surfaces. Another alternative is Tegaderm is a transparent medical dressing also manufactured by 3M. Tegaderm transparent dressing is typically used to cover and protect wounds and catheter sites. Advantages of Tegaderm include its breathability and conformation to non-flat surface.

In a preferred embodiment the substrate from will be a specifically designed layer that is frangible, serves as functional barrier yet is durable enough to withstand the printing process.

In an alternative embodiment the dye will contain particular materials for authentication and security, including but not limited to nano sized RFID chips, fluorescents and UV activated inks.

In an alternative embodiment, the printer could apply inks or other materials or substances to the CID to be used in connection with Laser, IR, UV light or any electromagnetic technology. Bioluminescent ink (light emitting from organic material), inks to print an OLED organic light-emitting diode (OLED) and other such materials can be used to interact with the device in any number of environments to enhance the capability or effectiveness of the product and also be used as a method of applying the device to an individual.

An alternative embodiment of the invention would have the tattoo function would include using a perforated barrier sheet which will serve as the substrate on which the CID construct will be built. In this embodiment the CID would be printed with a mirror image since the entire construct will be removed from the release paper and applied directly to the skin as apposed to flipping the construct and using a release agent.

However, as the CID is frangible, it would break apart and be destroyed if a removal attempt was made. The CID is designed to be nontransferable. Any attempt to remove the CID, whether in the sticker format or in contact to skin, intentional or non-intentional, will essentially destroy the CID. Any attempt to remove the RFID or any other machine read device form the skin after application would sever the circuit or antenna of said device thereby rendering it inactive and nonfunctioning The finished CID applied to the skin. Such CIDs may be removed by any technique used for the removal of temporary tattoos, such as rubbing with mineral oil, alcohol and so forth. Moisture may then be applied to paper layer, resulting in the release of the assembly of paper layer and release coating from the CID assembly, leaving behind the CID. In accordance with a preferred embodiment, CIDs are applied using a "peel packed" water impregnated foam pad designed to cover the temporary cutaneous identification device fully, and with sufficient aqueous solution that several temporary cutaneous identification devices can be applied with a single pad, but without so much aqueous phase as to drip or run. Such wet sponges, pads or the like may be packaged in any suitable container, such as double foil heat sealed containers of the type used to contain perfumes, condiments, and so forth. This pack may also include solutions that activate other processes in the ink like adhesive, UV pigments or the ink to change colors in certain conditions. The inventive identification badge can also be easily removed using a "peel pack" foam sponge impregnated with a solution capable of dissolving the adhesive of the inventive temporary cutaneous identification device without irritating the skin (e.g., mineral oil, baby oil, Detatchol™, etc.).

While and illustrative embodiment of the invention has been described, it is noted that various modifications will be apparent to those of ordinary skill in the art in view of the above description and drawings. Such modifications are within the scope of the invention, which is limited and defined only by the following claims.

What is claimed:

1. Apparatus for printing skin safe pigment on paper, applying a skin safe adhesive and covering said adhesive with a protective member to protect from the elements prior to the application process wherein said paper is adapted to release an image printed thereon onto skin in response to being dampened, wherein the apparatus is used at the point of service to manufacture a ready to apply cutaneous information device that is suitable for adhesion to a person's skin and able to be read visually or by an optical electronic device, wherein the information is comprises scannable variable data specific to the person and can be used to identify the person and where the cutaneous information device is rendered inoperable if the cutaneous information device is removed from the skin, wherein the device comprises a substantially white protective barrier interfacing with the skin to prevent contact between the skin and the pigment to prevent said pigment from being absorbed into the skin.

2. Apparatus as in claim 1, wherein a marking color and a background color are printed wherein the marking color and the background color are visibly different.

3. Apparatus as in claim 2, wherein said marking color is black and said background color is white.

4. Apparatus as in claim 3, wherein said printing is done with black and white toners.

5. Apparatus as in claim 3, wherein said printing is done with black, white and color pigments.

6. Apparatus as in claim 1, wherein said printing and said application of adhesive is done on a portion of an area of said paper dedicated to a cutaneous information device, leaving a peripheral portion to allow separation.

7. Apparatus according to claim 1, wherein the skin safe pigments would allow for printing of codes reading by an optical electronic device, electronic devices using near field communication technology such as RFID, NFC or UHF radio signals data processors such as circuits, microchips and microprocessors and security components for authentication.

8. Apparatus according to claim 1, wherein antimicrobial materials are added to one or more of the following elements: sheet, adhesive, or protective layer.

9. A method to manufacture a frangible non-transferable cutaneous information device (CID) using a printer, said device comprising biocompatible skin safe pigment and biocompatible adhesive comprising:
   a) printing a protective clear layer on the pigment;
   b) providing a release paper comprising paper treated with a material that would allow the pigment to be released;
   c) printing a quantity of the biocompatible skin safe pigment onto the treated release paper; and
   d) printing a quantity of the biocompatible adhesive onto the skin safe pigment,
   wherein the cutaneous information device is suitable for adhesion to a person's skin and able to be read visually or by an optical electronic device, wherein the data is scannable, variable and determined on site and the information is specific to said person and where the cutaneous information device is rendered inoperable if the cutaneous information device is removed from the skin and
   wherein the device comprises a substantially white protective barrier interfacing with the skin to prevent contact between the skin and the pigment to prevent said pigment from being absorbed into the skin.

10. A method according to claim 9, wherein the adhesive is included in the release layer, any of the protective coatings, or the formulation of the pigment.

11. A method according to claim 9, wherein a second protective layer is added resulting in a final construct of paper, release layer, a first protective layer, pigment layer, a second protective layer and adhesive.

12. A method according to claim 9, wherein the pigment and adhesive are mixed together and printing the pigment adhesive mixture onto the treated release paper.

13. A method according to claim 9, wherein adhesive can be applied or activated by solvent, water, UV light, electronic beam, or heat.

14. A method according to claim 9, wherein the clear layer is applied by a printer ribbon.

15. A method according to claim 9, wherein the one of more of the following non-contact machine readable devices are printed on the cutaneous information device including RFID tags, data codes, data matrix or bar codes, using metallic or conductive inks.

16. A method according to claim 15, wherein said non-contact machine readable electronic device devices are permanently destroyed if the cutaneous information device is removed from the skin.

17. A method according to claim 15 where the noncontact machine readable device is adapted to be printed on the device using metallic or conductive inks.

18. A method according to claim 15 where the noncontact machine readable device is severed and destroyed rendering it inoperable when the CID is removed.

19. A method according to claim 15 where the noncontact machine readable device is Magnetic Resonance Imaging (MRI) compatible.

20. A method according to claim 9, wherein the clear protective layer comprises adhesive.

21. A method of making a frangible, non-transferable cutaneous information device (CID) at point of service with variable data comprising a) a layer of adhesive adapted to be adhered to a surface such as human skin and b) a layer of skin safe pigment disposed on said layer of adhesive, comprising:
   1) printing with a substantially white pigment and a dark pigment onto a support member, and
   2) covering the printed pigment with said adhesive wherein once applied to skin, if removed, the device would not stay intact,
   wherein the CID is suitable for adhesion to a person's skin and able to be read visually or by an optical electronic device, wherein the information is variable and specific to the person and can be used to identify the person and where the cutaneous information device is rendered inoperable if the cutaneous information device is removed from the skin, and
   wherein the device comprises a substantially white protective barrier interfacing with the skin to prevent contact between the skin and the pigment to prevent said pigment from being absorbed into the skin.

* * * * *